(12) United States Patent
Dhamane et al.

(10) Patent No.: US 11,013,710 B2
(45) Date of Patent: May 25, 2021

(54) SYNERGISTIC COMPOSITIONS OF BIOACTIVE AGENTS FOR OPTIMIZING CELLULAR HEALTH

(71) Applicant: CELAGENEX RESEARCH (INDIA) PVT. LTD., Maharashtra (IN)

(72) Inventors: Dhiraj Dhamane, Kalyan (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 16/705,083

(22) Filed: Dec. 5, 2019

(65) Prior Publication Data

US 2020/0222351 A1 Jul. 16, 2020

(30) Foreign Application Priority Data

Dec. 5, 2018 (IN) .............................. 201821045886

(51) Int. Cl.
*A61K 31/205* (2006.01)
*A61K 31/706* (2006.01)
*A23L 33/175* (2016.01)
*A23L 33/15* (2016.01)
*A61P 29/00* (2006.01)
*A61K 31/4172* (2006.01)

(52) U.S. Cl.
CPC ............ *A61K 31/205* (2013.01); *A23L 33/15* (2016.08); *A23L 33/175* (2016.08); *A61K 31/4172* (2013.01); *A61K 31/706* (2013.01); *A61P 29/00* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,103,746 A | * | 8/2000 | Yarosh | A61P 43/00 514/398 |
| 6,900,338 B1 | | 5/2005 | Haj-Yehia | |
| 2001/0000472 A1 | * | 4/2001 | Henderson | A61K 31/357 424/725 |
| 2016/0067221 A1 | * | 3/2016 | Hseu | A61K 31/4172 514/392 |
| 2018/0071273 A1 | | 3/2018 | Horn | |

FOREIGN PATENT DOCUMENTS

| | | | | |
|---|---|---|---|---|
| WO | 1998036748 A1 | | 8/1998 | |
| WO | 2003099277 A1 | | 12/2003 | |
| WO | WO03/099277 | * | 12/2003 | ........... A61K 31/415 |
| WO | 2013101713 A1 | | 7/2013 | |
| WO | WO2016/149277 | * | 9/2016 | ........... A61K 31/455 |
| WO | WO2017/147058 | * | 8/2017 | ............. A61K 31/44 |
| WO | WO2018/191771 | * | 10/2018 | ........... A61K 31/196 |
| WO | 2019173159 A1 | | 9/2019 | |

OTHER PUBLICATIONS

DeBeradinis et al., "Cellular Metabolism and Disease: What Do Metabolic Outliers Teach Us?" Cell vol. 148 pp. 1132-1144 (Year: 2012).*
Maejima et al., "Oxidative Stress and Cardiac Muscle" chapter 23 of Fundamental Biology and Mechanisms of Disease vol. 1, pp. 309-322 (Year: 2012).*
Taguchi et al., "Keap1 degradation by autophagy for the maintenance of redox homeostasis" PNAS vol. 109 No. 34 pp. 13561-13566 (Year: 2012).*
Hybertson et al., "Oxidative stress in health and disease: The therapeutic potential of Nrf2 activation" Molecular Aspects of Medicine vol. 32 pp. 234-246 (Year: 2011).*
Sporn et al., "NRF2 and cancer: the good, the bad and the importance of context" Nature Reviews vol. 12 pp. 564-571 (Year: 2012).*
Wei et al., "Nicotinamide mononucleotide attenuates brain injury after intracerebral hemorrhage by activating Nrf2/HO-1 signaling" Scientific Reports vol. 7 No. 717 pp. 1-13 (Year: 2017).*
Diguet et al., "Nicotinamide Riboside Preserves Cardiac Functions in a Mouse Model of Dilated Cardiomyopathy" European Journal of Heart Failure vol. 19 Suppl S1, p. 24 abstract 173 (Year: 2017).*
Wang et al., "Nicotinamide riboside attenuates alcohol induced liver injuries via activation of SirT1/PGC-1α/mitochondrial biosynthesis pathway" Redox Biology vol. 17 pp. 89-98 (Year: 2018).*
Kaminskyy, V. et al., "Cell Death-Based Treatment of Various Diseases" Cell Death and Disease, vol. 9, Article No. 110 (2018).

(Continued)

*Primary Examiner* — Eric Olson
(74) *Attorney, Agent, or Firm* — Maschoff Brennan

(57) ABSTRACT

The present invention discloses herein a synergistic composition(s) of bioactive agents for optimizing cellular health. Particularly, a synergistic bioactive composition for optimizing cellular health, wherein the composition comprising therapeutic blend of betaine of thiol histidine and sirtuin activator(s) or salts thereof present in the ratio of 1:0.5 to 1:90, along with pharmaceutically acceptable excipients. In another embodiment, the invention discloses novel synergistic nutritional composition comprising synergistic combination of bioactives L-ergothioneine and nicotinamide mononucleotide chloride present in the ratio ranges from 1:1 to 1:80. The present invention provides promising and effective nutritional composition for improving cellular health by regulating expression of transcriptional factor, pro-inflammatory cytokines, and reducing cell apoptosis, ROS level and DNA damage in the cell.

12 Claims, 5 Drawing Sheets

(56) References Cited

OTHER PUBLICATIONS

Xu, D. et al., "The Rolf of Nrf2 in Liver Disease: Novel Molecular Mechanisms and Therapeutic Approaches". Frontiers in Pharmacology. 2018; 9: 1428.
Hussain, T. et al., "Modulatory Mechanism of Polyphenols and Nrf2 Signaling Pathway in LPS Challenged Pregnancy Disorders" Oxididative Medical and Cellular Longevity. 2017; 2017: 8254289.

* cited by examiner

Figure:1
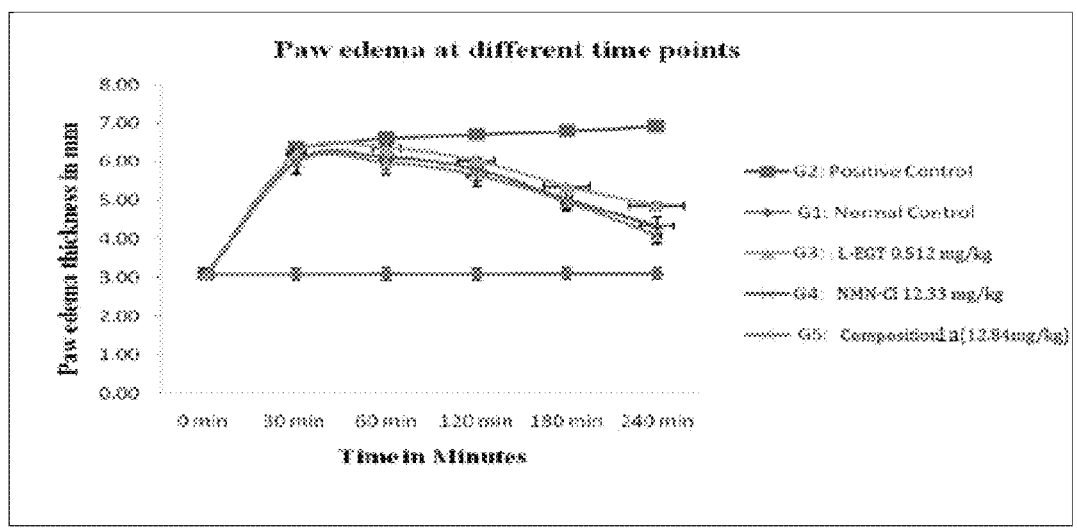

Figure: 2a
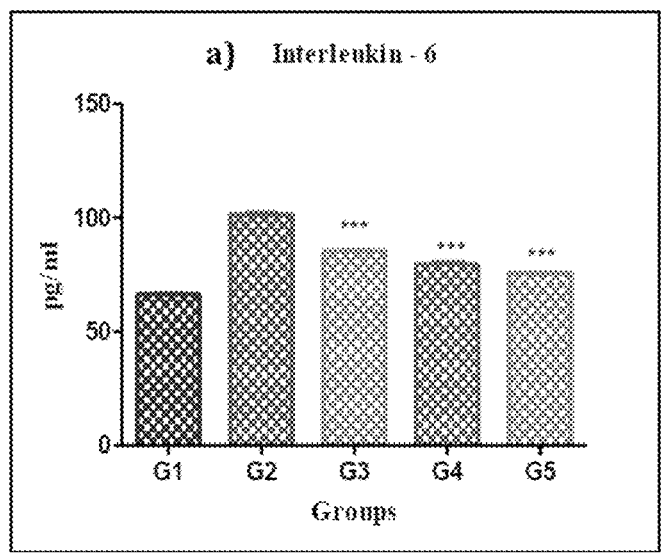
Figure: 2b
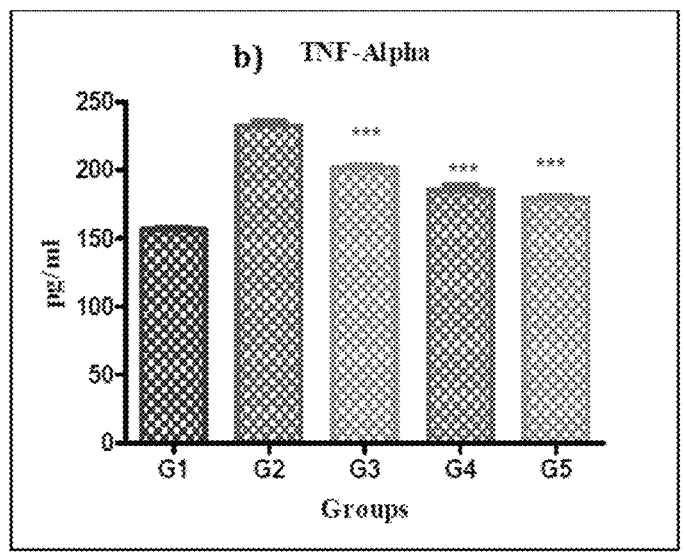

Figure: 3
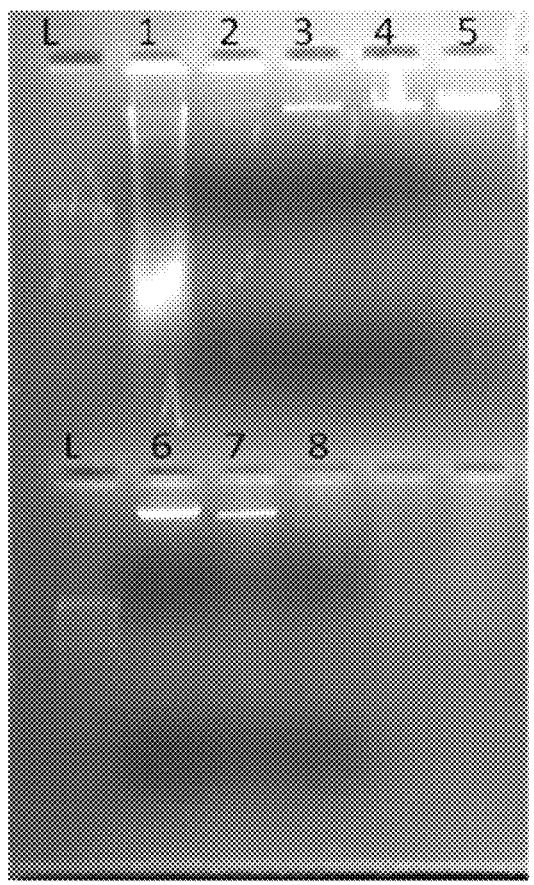

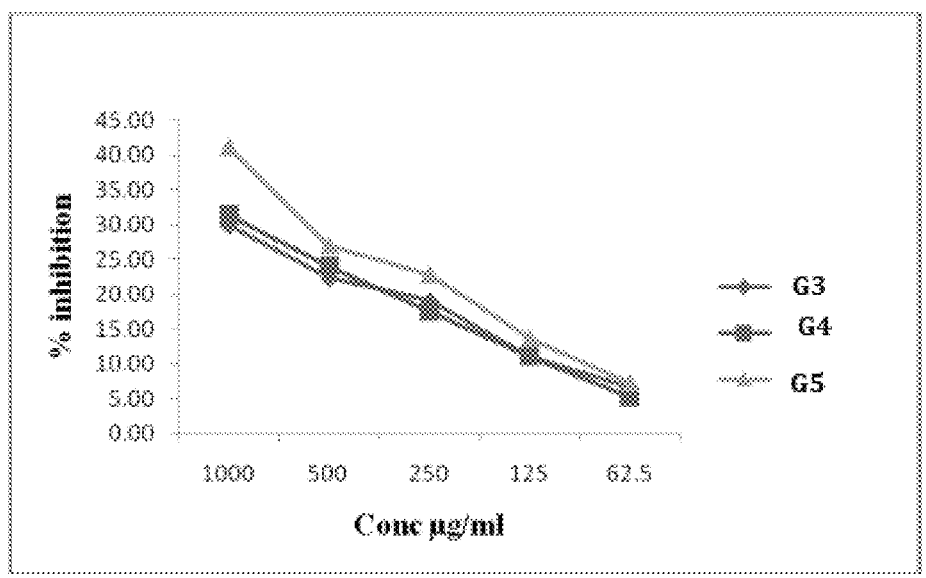
Figure: 4

Figure: 5
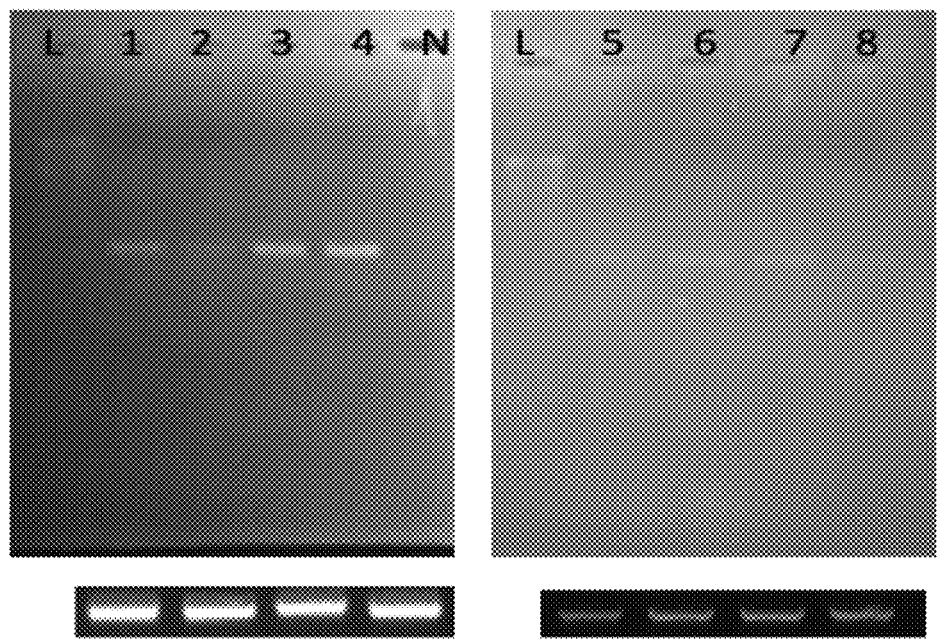

SYNERGISTIC COMPOSITIONS OF BIOACTIVE AGENTS FOR OPTIMIZING CELLULAR HEALTH

TECHNICAL FIELD

The present invention relates to synergistic compositions of bioactive agents for optimizing cellular health. Particularly, the invention relates to synergistic compositions comprising therapeutically effective amount of bioactive agents, which are selected from the group consisting of betaine of thiol histidine and sirtuin activator(s).

More particularly, the instant synergistic compositions are composed of specific bioactive agents in effective amount, wherein betaine of thiol histidine is L-Ergothioneine (L-EGT); sirtuin activator is Nicotinamide mononucleotide (NMN) and along with pharmaceutically acceptable excipients.

Further the present invention provides promising and effective nutritional composition for cellular protection by reducing inflammation, cell apoptosis, ROS level and DNA damage. Further it regulates expression of transcriptional factor such as Nuclear erythroid 2-related factor 2 (Nrf2).

Moreover, the present nutritional composition is useful for treating pregnancy complications, liver & kidney diseases.

BACKGROUND AND PRIOR ART

In an ideal environment, cellular health would automatically allow each of our cells to function, reproduce, and communicate properly. Cells would have ample nourishment and protection and be capable of completing multiple processes necessary for total and complete health.

Unfortunately, we live in a contaminated, polluted world, where the natural mechanisms designed to ensure cell health are affected or damaged. High-stress lifestyles, processed foods, chemicals in cleaning and personal care products, and excessive use of prescription drugs bombard our cells and make it difficult for these tiny but essential parts of our total health to perform properly.

Cells are the basic building blocks of living things. The human body is composed of trillions of cells, all with their own specialised function. Cells provide structure for the body, take in nutrients from food and carry out crucial functions. Cells are characterized by their ability to grow, reproduce, respond to external stimuli and perform the different metabolic processes.

Cells within the human body contain thousands of genes, proteins and other chemicals enclosed within cellular membranes. Each cell responds to chemical signals from the body or the environment and modifies its behavior in response to signals. Cellular diseases occur when cells dysfunction; this may include the development of too many cells, deficiencies in existing cells or dysfunction or loss of essential cells. Cellular diseases vary in severity and the types of cells they affect, sometimes proving fatal.

The cell is made up of a protoplasmic mass surrounded by the cell membrane. The protoplasm is differentiated into a nucleus and cytoplasm. Cytoplasm contains a group of functional cellular structures called cell organelles, such as mitochondria, ribosome, nucleus, cytoplasm, DNA, plasma membrane etc. These organelles carry out tasks such as making proteins, processing chemicals and generating energy for the cell.

Reactive oxygen species (ROS) are derivatives of oxygen that are more reactive than molecular oxygen. It is used as a collective term for reactive forms of oxygen, including both radical and non-radical species that is involved in the initiation and/or propagation of chain reaction.

A primary ROS is superoxide ($O2^-$), which is formed by one-electron reduction of molecular oxygen. Hydrogen peroxide ($H_2O_2$) is produced by reduction of $O2^-$ through dismutation. Hydroxyl radical ($OH^-$) arises from electron exchange between $O2-$ and $H_2O_2$ via the Harber-Weiss reaction or it is also generated by the reduction of $H_2O_2$ by the Fenton reaction. When generated under strictly regulated conditions, these ROS, in particular $O2-$ and $H_2O_2$, may act as signaling molecules that mediate physiological processes, such as cell growth, differentiation, metabolism, and survival of cardiomyocytes. This type of intracellular signaling pathway is termed "redox signaling". On the other hand, excess production of ROS damages DNA, protein, and lipids, thereby causing cell death (apoptosis), which is the indication of several cellular diseases. (*Fundamental Biology and Mechanisms of Disease* Volume 1, 2012, Pages 309-322)

Typically the formation of reactive oxygen species (ROS) is including free radicals such as superoxide anion, hydrogen peroxide, and formation of hydroxyl radical is one of the prominent causes of cellular DNA damage.

DNA which is continuously attacked by reactive species can affect its structure and function severely. Structural modifications to DNA mainly arise from modifications in its bases that primarily occur due to their exposure to different reactive species. Apart from this, DNA strand break, inter- and intra-strand crosslinks and DNA-protein crosslinks can also affect the structure of DNA significantly. These structural modifications are involved in mutation, cancer and many other diseases.

Generally, ROS are generated by exogenous sources such as pollutants, tobacco, smoke, drugs, ozone, pesticides, organic solvents, alcohol, xenobiotics, or radiation.

But they are produced intracellularly (endogenous) also through multiple mechanisms and depending on the cell and tissue types such as mitochondria, endoplasmic reticulum peroxisomes, phagocytes, cytochrom P, reaction of metal ions, NADPH oxidase, NO synthase, Xanthine oxidase etc.

'ROS' production by mitochondria can lead to oxidative damage to mitochondrial proteins, membranes and DNA, impairing the ability of mitochondria to synthesize ATP and to carry out their wide range of mitochondrial functions.

Enhanced level of ROS can cause damage to biomolecules such as lipids, proteins and DNA. These reactions can alter intrinsic membrane properties like fluidity, ion transport, loss of enzyme activity, protein cross-linking, inhibition of protein synthesis, DNA damage, and so forth ultimately resulting in cell death (apoptosis). DNA damage activates certain pivotal proteins that lead to amplification and propagation of a signal, ultimately resulting in cellular outcomes such as mitophagy and apoptosis. Importantly, low levels of DNA damage stress may stimulate mitophagy and antagonize apoptosis, whereas high levels of stress inhibit mitophagy and stimulate apoptosis. Malfunctioning in cell death pathways at the molecular level can be linked to the pathogenesis not only of cancer, but also other diseases of enormous social importance, such as HIV, atherosclerosis, ischemia, infection, inflammation, autoimmune, and neurological disorders, cardiovascular diseases [*Cell Death & Disease* volume 9, Article number: 110 (2018)].

Because of the multifunctional roles of ROS, it is necessary for the cells to control the level of ROS firmly to avoid any oxidative damage.

Several mechanisms are responsible for the protection of the cells from potential cytotoxic damage caused by free radicals. Cells have developed various enzymatic and nonenzymatic defense systems to control excited oxygen species, however, a certain fraction escapes the cellular defense and may cause permanent or transient damage to nucleic acids within the cells, leading to such events as DNA strand breakage and disruption of Ca2+ metabolism.

Scavenging or detoxification of excess ROS, achieved by antioxidative defense mechanisms, comprises nonenzymic as well as enzymic antioxidants. The enzymic antioxidants include superoxide dismutase (SOD), catalase (CAT), guaiacol peroxidase (GPX), enzymes of ascorbate-glutahione (AsA-GSH) cycle such as ascorbate peroxidase (APX), monodehydroascorbate reductase (MDHAR), dehydroascorbate reductase (DHAR), and glutathione reductase (GR); whereas Ascorbate (AsA), glutathione (GSH), carotenoids, tocopherols, and phenolics serve as potent nonenzymic antioxidants within the cell.

However, the uses of enzymatic and nonenzymatic antioxidants are associated with certain limitations or disadvantages, which could not give desired result for enhancing cellular metabolic pathway, such as SOD in free form has reduced half-life in the bloodstream; in short it has low bioavailability.

It is observed that thiol mediated compounds show significant result for regulating level of ROS, where the changes in the thiol redox state of proteins impacts on cellular function. ROS and redox biology of thiol are tightly interlinked to form a complex analog redox.

Glutathione (GSH) is capable of preventing damage to important cellular components caused by reactive oxygen species such as free radicals, peroxides, lipid peroxides, and heavy metals. However, it needs higher dose and particular route of administration. Further GSH is frequently supplemented with nutrients like curcumin, vitamins, silymarin to boost the production of GSH in the body.

Oxidative damage to cellular macromolecules is supposed to cause of development of many pathological states and aging. The agents responsible for this damage are generally thought to be reactive oxygen species, such as superoxide, hydrogen peroxide, and hydroxyl radical. The main source of reactive species production within most cells is the mitochondria.

Free-radical damage to the mitochondria is the fundamental cause of aging. Mitochondrial dysfunction is a factor in diseases that involve energy balance, such as age- and disease-related muscle wasting, heart failure, chronic fatigue, Alzheimer's, Parkinson's, even diabetes and obesity.

Consequently, the generation of cellular Reactive Oxygen Species (ROS) induced by both endogenous and exogenous stimuli lead to oxidative damage to cell proteins, membranes and DNA, impairing the ability of mitochondria to synthesize ATP and to carry out their wide range of metabolic functions that contributes to a wide range of pathologies. In addition, mitochondrial ROS may act as a modulatable redox signal, reversibly affecting the activity of a range of functions in the mitochondria, cytosol and nucleus.

Mitochondrial ROS attack DNA readily, generating a variety of DNA damages such as oxidized bases and strand breaks. Because damage to mitochondria is believed to be the cause or an important factor in chronic diseases, such as cancer, diabetes, cataract, neurodegenerative disease, porphyrias, cardiovascular disease, and also a contributor to the complications of aging.

It is further observed that oxidative stress induces pregnancy disorders or impairment in the fetal or uterine life. Studies reported that strong maternal uterine antioxidant environment could prevent pregnancy disorders and abnormal birth outcomes and could also prevent other complications later in life which might initiate from embryonic stage. More molecular evidences are required for antioxidant/ inflammatory events from fertilization to parturition during pregnancy. So there is need to find out new roadmap to researchers for therapeutic intervention which could subsequently improve human and animal fertility or oxidative stress-induced pregnancy insults.

Further it is observed that oxidative stress and inflammation are the most important pathogenic events in liver diseases. In liver injuries, the unregulated production of free radicals and/or ROS leads to damage of important biomolecules and cells and generation of proinflammatory genes. Nrf2 is the master regulator of the primary means of cellular defense through mediation of antioxidant response, antiinflammatory and cytoprotective properties, wherein dysregulation of Nrf2 activity has been revealed to correlated with the development of chronic inflammatory diseases. It is further reported that a potent activator of the Nrf2 pathway, leads to enhanced autophagy in hepatocytes, which results in increased clearance of damaged mitochondria, and reduced ROS production leading to reductions hepatocyte injury [*Front Pharmacol.* 2018; 9: 1428].

Oxidative stress also activates NF-κB, PPAR-γ, AP-1, and JNK pathways which accounts for pathological conditions in pregnancy disorders. In addition, NF-κB is responsible for transcription of several proinflammatory cytokines which are known to induce pregnancy disorders and adverse outcomes such as TNF-α, IL-1β, IL-6, and PGF2E. Importantly, stimulation of Nrf2 signals plays a crucial role in ameliorating pregnancy insults. It was further counted that oxidative stress is the major contributing factor, for pathogenesis of cellular disorders.

Particularly Nrf2 is very sensitive to maternal immune status and is responsible for fetal growth and survival through maintaining fetus desirable placental environment; later, of the placenta was decreased following delivery. Intriguingly Nrf2 also provides protection during uterofetal life against a variety of stressors. The inappropriate function of Nrf2 protein could lead to inducing numerous pregnancy disorders [*Oxid Med Cell Longev.* 2017; 2017: 8254289].

There are different nutrients available in the art that works as ROS scavenger or useful as prophylactic agent for regulating mitochondrial function.

US20180071273A1 discloses nutritional compositions comprising combination of nicotinamide riboside chloride, acetyl 1-carnitine, apple extract, lipoic acid, pterostilbene for treating mitochondrial energy disorders or diseases.

U.S. Pat. No. 6,900,338B1 discloses lipoic acid compounds having scavenging and anti-ROS properties and pharmaceutical composition thereof for treatment of conditions associated with oxidative stress or free radical injury.

The oxidative stress is the biological systems as a means to characterize the total burden of potentially harmful reactive oxygen species that are present in tissues as a consequence of routine cellular oxidative metabolism of both endogenous and exogenous compounds.

WO2013101713A1 discloses nutritional composition containing ergothioneine and vitamin D; for controlling or neutralizing free radical damage to protect against oxidative skin damage in mammal. Similarly WO1998036748A1 discloses liposome-encapsulated L-ergothioneine for protecting mitochondria from damage caused by radiation, radicals and reactive oxygen species.

Further US20160067221A1 discloses the effect of the ergothioneine on a content of reactive oxygen species (ROS) induced by the ultra violet stimulation.

WO2019173159A1 discloses synergistic combination of vitamin C and ergothioneine, derivative for improving cellular level of vitamin C WO2003099277A1 discloses combination of L-ergothioneine with vitamins C or E for treating diabetes-associated embryopathy.

In the light of above prior arts, it is evident that thiol containing moiety mitigate oxidative damage caused due to ROS; however none of the prior arts referred in the specification acknowledge the synergistic effect of bioactive agents that exhibit scavenging of excessive ROS produced in the cell and concurrent repairing of damage DNA through suitable metabolic pathway.

Therefore, a need arises for bioactive agents that effectively improve human health through normalization and optimization of the damaged cells at first level. Eventually better health with longer lifespan can be achieved.

The present inventors have addressed certain limitations and deficiencies associated with existing pharmaceutical compositions.

The researchers have found that thiol containing amino acid has powerful antioxidant activity, which protect DNA from the damage caused by oxidative stress. The antioxidant can also protect the mitochondria from the effects of the free radicals produced during ATP manufacture.

Research on animals suggests that ergothioneine supplementation increases mitochondrial membrane function and metabolic activity and reduces the potential for oxidative damage. Further sirtuin activator, serves as a precursor to NAD+, a compound that is important in the electron transport for energy production, and inhibits DNA strands from rupturing. Supplementation of nicotinamide mononucleotide has been found to reduce DNA damage in human white blood cells.

Accordingly by performing exhaustive research and experiments the inventors have successfully developed synergistic composition of thiol mediated amino acid with NAD compound for optimizing cellular health that ultimately improve human health and longevity, particularly human fetal and pregnancy or uterine and kidney and liver health.

Objective

The primary object of the invention is to provide bioactive composition comprising active moieties that regulate excessive ROS production in the cell by reducing inflammation and simultaneously or subsequently repairing damaged DNA so that overall cellular function is improved in a subject need thereof.

Another object of the invention is to cater therapeutically active composition of bioactive agents in suitable dosage form that gives synergistic effect to regulate oxidative damage in the cell.

Further object of the invention is to provide environmentally safe, non-toxic, cost effective nutritional composition for cellular health improvement.

SUMMARY

To meet the above objectives, the inventors of the instant invention carried out thorough experiments to establish the significant effect of the active moieties present in the composition that improve the cellular health in a subject in need thereof.

In an aspect, the invention provides synergistic compositions of bioactive agents/compounds for optimizing cellular health.

In another aspect, the invention relates to synergistic compositions comprising therapeutically effective amount of bioactive agents, which are selected from the group consisting of betaine of thiol histidine and sirtuin activator(s), optionally antioxidant or fatty acid transporter(s);

wherein betaine of thiol histidine is ergothioneine and sirtuin activator is nicotinamide mononucleotide.

In yet another aspect, the instant invention provides compositions comprising synergistic combination of L-ergothioneine (L-EGT) and nicotinamide mononucleotide (NMN) in a subject suffering from cellular diseases or malfunctioning of organelle such as neurodegenerative diseases, liver diseases, kidney diseases, pregnancy complications, multiple sclerosis, diabetes, obesity, cardiovascular disorders, cancer and like thereof.

In another aspect, the invention relates to synergistic composition of L-ergothiotheine and nicotinamide mononucleotide; wherein L-ergothioneine act as ROS scavenger or inflammation suppressor and nicotinamide mononucleotide act as DNA repair facilitator.

In one more aspect, the invention provides synergistic bioactive compositions, wherein L-EGT regulates Nrf2 expression and decreases inflammation triggered by ROS; concomitantly NMN repairs DNA damage in liver and kidney and reduces cell apoptosis.

In yet another aspect, the invention relates to synergistic compositions comprising combination of ergothioneine present in the range of 1 to 250 mg and nicotinamide mononucleotide present in the range of 1 to 500, along with pharmaceutically acceptable excipients/carriers.

In yet another aspect, the invention relates to synergistic composition of ergothioneine and nicotinamide mononucleotide, wherein the production of excessive ROS formation is regulated by the thiol moiety of ergothioneine, particularly transport of ergothioneine by OCTN1 protects cells against oxidative damage and subsequently reduces inflammation.

In yet another aspect, the invention relates to synergistic composition of ergothioneine and nicotinamide mononucleotide, wherein nicotinamide mononucleotide is NAD precursor that actively repairs the oxidative damage in the cell, particularly DNA repairing mechanism.

In another aspect the instant synergistic composition is useful for improving cellular health, particularly human fetal and pregnancy or uterine and kidney and liver health.

Abbreviations

L-EGT: L-Ergothioneine
ETT: Ergothioneine transporter
OCTN1: Organic cation/Carnitine transporter 1
NMN: Nicotinamide mononucleotide
NAD: Nicotinamide adenine dinucleotide
SIRT1: Silent information regulator T1 (sirtuin family)
OCTN1: Organic cation/carnitine transporter 1
Nrf2: Nuclear factor erythroid 2-related factor 2
AAPH: 2,2'-azobis(2-amidinopropane)dihydrochloride

BRIEF DESCRIPTION OF FIGURES

FIG. 1 depicts effect of test substances on paw edema at different time points of measurement FIGS. 2a and 2b depict effect of test substances on serum a) IL-6 and b) TNF-Alpha levels in rats FIG. 3 depicts DNA ladder assay of test substances on HepG2 cell line; L=100 bp Ladder, Lane 1=AAPH (1 mM), Lane 2=cell control, Lane 3=G3 (250 µg/ml), Lane 4=G4 (250 µg/ml), Lane 5=G5 (5:125-250 µg/ml), Lane 6=G3+AAPH, Lane 7=G4+AAPH, Lane 8=G5+AAPH FIG. 4 depicts Graph of cytotoxic effect of test substance on HepG2 Cell line.

FIG. 5 depicts effect of the Test Substances (G3, G4, G5) on Nrf2 transcripts in HepG2.-L: 100 bp marker, Lane 1: CA+G3+G4, Lane 2: Cell Control, Lane 3: G3 Lane 4: Caffeic acid (20 µM), Lane 5: G5, Lane 6: CA+G3, Lane 7: CA+G4, Lane 8: G4

DETAILED DESCRIPTION

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions or terms used herein have the same meaning as commonly understood by one of ordinary skill in the art to which embodiments of the invention pertain.

In describing and claiming the embodiments of the present invention, the following terminology will be used in accordance with the definitions set out below which are known in the art.

The singular forms "a," "an," and "the" include plural reference unless the context clearly dictates otherwise. Also the term 'composition' does not limit the scope of the invention it may include multiple compositions illustrations to establish best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, alkali or alkaline earth metal salts, as well as solvates, co-crystals, polymorphs, isomers, enantiomers, congeners and like thereof.

In preferred embodiment, the present invention provides synergistic composition of therapeutically active agents.

Particularly, the invention provides synergistic combination of betaine of thiol histidine and sirtuin activator(s), optionally fatty acid transporter(s) in therapeutically effective amount.

In another preferred embodiment, the invention discloses the synergistic combination of ergothioneine and nicotinamide mononucleotide, optionally acetyl-1-carnitine or pharmaceutically acceptable salts thereof along with pharmaceutically acceptable carriers.

In one embodiment, the invention provides nutritional composition comprising thiol mediated moiety called L-Ergothioneine or L-EGT which act as ROS scavenger/inflammation suppressor.

In the present invention the thiol mediated active moiety 'Ergothioneine' can also be referred as L-Ergothioneine; L-EGT; L-(+)-Ergothioneine (ERG); 2-mercaptohistidine trimethylbetaine, 2-Mercapto-L-histidine betaine; S-alpha-carboxy-2,3-dihydro-N,N—N-trimethyl-thioxo-1H-imidazole-4-eth-anaminium hydroxide; Thiasine; Thiazine; Thiolhistidinebetaine; Thioneine. Hereinafter the L-Ergothioneine is referred as 'EGT' or L-EGT.

'Ergothioneine' is a naturally occurring amino acid and is a thiourea derivative of histidine, containing a sulfur atom on the imidazole ring. It is having chemical formula $C_9H_{15}N_3O_2S$.

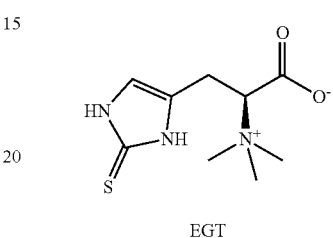

EGT

'EGT' is a thiol-containing antioxidant amino acid at physiological pH. It is widely distributed in both the plant and animal kingdoms. Mammals acquire EGT solely through their diet. Foods such as mushrooms, black beans, red meat and oats are rich in EGT. As human body cannot synthesize the ergothioneine, hence the ergothioneine is only taken from dietary supply.

EGT is acknowledged as a safe and effective antioxidant for preventing lipid oxidation-induced quality changes in food and various diseases associated with oxidative stress. This water-soluble antioxidant has the ability to scavenge hydroxyl and peroxynitrite radicals as well as activated oxygen species, such as singlet oxygen. Ergothioneine is a powerful scavenger of hydroxyl radicals.

Unlike other antioxidants such as glutathione or N-acetyl-L-cysteine (NAC, a precursor of glutathione), EGT is characterized by its slow degradation and resistance to disulfide formation. EGT disulfide formation occurs only at low pH in the presence of $Cu^{++}$ or $H_2O_2$, but not under physiological conditions. Specific organic cation transporter [OCTN1 or ETT] is an integral membrane protein which transports EGT, depending on the concentration of Na and W. Further EGT accumulates in the organelle, where OCTN1 is expressed and protects the cell from damage by ROS generated through inflammation. Ergothioneine is the best known substrate of ETT. The ETT is a protein integrated into the cell membrane. It is noteworthy that transport of ergothioneine by OCTN1 protects cells against oxidative damage and thus reduces the inflammation caused by the secretion of cytokines.

Furthermore L-EGT participates in the production of ATP as part of the electron transport chain and protects the cell/organelles against oxidative damage.

Reactive oxygen species (ROS) and mitochondria play an important role in apoptosis induction under both physiologic and pathological conditions. Interestingly, mitochondria are both source and target of ROS.

In another embodiment, the redox mechanism of thiol group of L-EGT impacts the cellular function, where during redox signaling, $H_2O_2$ oxidizes the thiolate anion to sulfenic form (Cys-SOH) causing allosteric changes within the protein that alter its function. The sulfenic form can be reduced to thiolate anions by the disulfide reductases, thioredoxin (Trx) and glutaredoxin (Grx), to return the protein function to its original state.

In another embodiment, the invention provides the active moiety L-EGT improves Nrf2 activity or expression and reduces cell/tissue inflammation by scavenging or reducing production of ROS.

In another embodiment, the synergistic composition comprises therapeutically effective amount of L-EGT or pharmaceutically acceptable salts thereof, wherein L-EGT is present in the range of 1-250 mg, preferably in the range of 1-100 mg.

In the synergistic bioactive compositions L-ergothioneine is present in the range of 0.1% to 70% by wt of total blend or composition, preferably 0.5 to 50% w/w.

In another preferred embodiment, the invention relates to sirtuin activator for repairing DNA damage caused due to oxidative stress or excessive ROS, wherein the sirtuin activator is nicotinamide mononucleotide (NMN) or pharmaceutically acceptable salts thereof, which repairs the damage DNA through suitable mechanism and thus improves the cellular function.

The pharmaceutically acceptable salt of NMN comprises chloride, bromide, sodium, disodium, triflate, acetate and like thereof, preferably the instant composition comprises beta-NMN as SIRT1 activator.

Nicotinamide mononucleotide ("NMN","NAMN") is also referred as beta-Nicotinamide mononucleotide (β-NMN), beta-NMN, beta-nicotinamide ribose monophosphate, Nicotinamide mononucleotide (NMN) or Nicotinamide-1-ium-1-β-D-ribofuranoside 5'-phosphate, nicotinamide ribonucleotide is a nucleotide derived from ribose and nicotinamide. It is having molecular formula $C_{11}H_{15}N_2O_8P$).

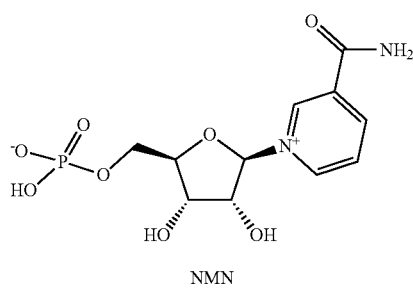

NMN

In certain embodiments, cells treated with a nicotinamide mononucleotide a compound that augments level of intracellular NAD+.

Nuclear DNA damage is regarded as a major culprit in cellular diseases. The unrepaired DNA damage can result in pathological levels of nucleus-to-mitochondria signalling (NM signalling), which may aggravate disease progression. As DNA is constantly assaulted by both endogenous (for example, reactive oxygen species and hydrolysis) and exogenous (such as ultraviolet and ionizing radiation) stresses, cells have evolved several DNA repair pathways to maintain the integrity of DNA. Major DNA repair pathways in the nucleus include direct reversal (DR) of the lesion (usually methylation), base excision repair (BER), mismatch repair (MMR), nucleotide excision repair (NER; comprising global genome NER and transcription-coupled NER), double-strand break repair (DSBR, which includes non-homologous end-joining (NHEJ) and homologous recombination (HR)) and inter-strand crosslink repair (ICLR).

In another embodiment, the nicotinamide mononucleotide (NMN), repair DNA damage via histone deacetylation, through the deacetylation of the two histone acetyltransferases, TIP60 and MOF, which are able to acetylate histone H4. Deacetylation of these two proteins promotes their ubiquitin-dependent degradation affecting DNA double-strand break (DSB) repair either through the repression of repair or affecting the choice of repair mechanism (i.e. homologous recombination or non-homologous end joining).

In another embodiment, the promotion of DNA and protein repair by NMN allows increased cell proliferation, differentiation and viability and thereby improves the cellular health. Moreover the NMN moiety works synergistically such that it controls DNA damage and cell apoptosis in the affected area, such as liver, kidney, uterus, placenta.

In another embodiment, the synergistic composition comprises therapeutically effective amount of NMN or pharmaceutically acceptable salts thereof, wherein NMN is present in the range of 1-500 mg, preferably 1 to 250 mg of total composition, particularly NMN salt is present in the range of 0.1-98%, preferably 0.5-98% w/w of total blend or composition.

In yet another embodiment, the invention provides nutritional compositions wherein the effective amount of L-EGT enhances the activity or expression of Nrf2 and mitigates stress induced inflammation, wherein the NMN improves or controls DNA damages triggered by oxidative stress.

It is observed that Nrf2 knocked out subjects show foetal growth suppression and foetal DNA insult resulting into neurological deficit, pre-term delivery, IUGR. Nrf2 down regulation shown to down regulate m-RNA and meiosis genes, delayed oocyte progression & decreased number of primordial follicles.

Nrf2 is essential transcription factor that regulates detoxifying and antioxidant defense gene expression in liver and kidney cells. Stimulation of Nrf2 signals plays a crucial role in ameliorating pregnancy insults, wherein Nrf2 activation can also be induced by controlling DNA damage or cell apoptosis.

Accordingly, to the invention Nrf2 signalling pathway regulates early embryonic loss, adverse birth outcomes, pregnancy complications such as pre term birth, intrauterine growth restriction (IUGR), early pregnancy loss, neural tube defects (NTD), intra-Uterine Death (IUD), pre-eclampsia (PE).

The activated Nrf2 ameliorates EL-OH induced neural crest apoptosis in foetus, reduces Trophoblast apoptosis triggered by inflammation, exhibits protective effects towards oxidative insult during early pregnancy development (neural crest formation), decreases DNA damage in liver & decreased serum alanine aminotransferase (ALT), lactic acid dehydrogenase (LDH), liver necrosis, aspartate aminotransferase (AST), interleukin 1 beta (IL-1β), Interleukin 6 (IL-6), tumour necrosis factor alpha (TNF alpha) & ROS levels.

In further embodiment, the present synergistic composition comprising of effective amount of L-ergothionine & NMN up regulate Nrf2 level and simultaneously reducing inflammation, and DNA damage. More particularly the composition comprising combination of L-ergotionine & NMN exhibit synergistic & more superior and significant effects such as increases Nrf2 expression; reduces inflammation by controlling cytokines IL-6, TNF-Alfa expression; reduces cell apoptosis; DNA damage and controls ROS levels.

Antioxidant helps to transport fat, particularly long-chain fatty acids, into the mitochondria of cells and get oxidized to generate adenosine triphosphate, or ATP.

In another optional embodiment, the invention discloses effective amount of antioxidant enhances cellular function by reducing increased mitochondrial oxidant production, it add-on Nrf2 activity, anti-inflammatory activity.

In another embodiment, the bioactive agents used in the instant composition are not limited to ergothioneine, nicotinamide mononucleotide and optionally antioxidant, but it also comprising therapeutically active agents that influence physiological or cellular activities in the animals or humans. The bioactive compounds or agents include an extremely heterogeneous class of compounds such as polyphenolic compounds, carotenoids, tocopherols, phytosterols, and organosulfur compounds with different chemical structures (hydrophilic or lipophilic), distribution in nature (specific to vegetable species or ubiquitous), range of concentrations both in foods and in the human body, possible site of action, effectiveness against oxidative species, and specificity and biological action (Carbonell-Capella et al., 2014; Porrini & Riso, 2008).

The consumption comprising of such bioactive agents in effective amount useful for enhancing cellular metabolic pathways and assists in normalization of cellular functions and optimization of cellular health.

Bioactive agents can protect against diseases via several mechanisms, but it is believed that the antioxidant activity is extremely important for protection against diseases related to oxidative stress.

In another embodiment, the oxidative stress triggered by ROS is controlled by regulating or modulating Nrf2 and inflammatory cytokine expression and DNA fragmentation.

An "effective amount of bioactive agent" is an amount sufficient to prevent, treat, reduce, and/or ameliorate the symptoms and/or underlying causes of cellular diseases.

In the context of the present invention, the terms "treatment" and the like refer to alleviate, slow the progression, prophylaxis, attenuation, or cure of existing cellular diseases. The instant composition is used for treating cellular diseases in a subject need thereof, means either the administration of the remedy to prevent the onset or occurrence of cellular disorders, or treat already present cellular disorders.

The 'subject in need thereof' pertains to subject preferably mammal, more preferably human suffering from cellular disorders or in a subject to prevent occurrence of cellular diseases.

In further embodiment, the composition comprises synergistic combination of L-EGT and NMN chloride, which are present in the ratio of 1:1 to 1:80; particularly 1:1 to 1:60. In yet another preferred embodiment, the invention relates to synergistic compositions comprising combination of L-ergothioneine which is present in the range of 1 to 250 mg and nicotinamide mononucleotide present in the range of 1 to 500 mg along with pharmaceutically acceptable excipients/carriers.

Particularly, the instant synergistic compositions comprise combination of ergothioneine present in the range of 1 to 100 mg and nicotinamide mononucleotide present in the range of 1 to 250 mg along with pharmaceutically acceptable excipients/carriers.

In some embodiment, the invention provides the synergistic nutritional composition of bioactives, wherein the composition comprises combination of bioactives L-ergothioneine and beta-nicotinamide mononucleotide present in the ratio of 1:0.5 to 1:90.

According to the invention, the synergistic nutritional composition of bioactives, wherein the amount of L-ergothioneine is in the rage of 1 to 10%; the amount of beta-nicotinamide mononucleotide is in the range of 10 to 80% by wt of total composition.

In another embodiment, the invention discloses synergistic composition which is useful for optimizing cellular health.

The term 'cellular optimization' does not limit the scope of the invention. It relates to nourishment of the body with desired nutrients for healthy cellular function. It is achieved by either maintaining diet or administering suitable nutrient composition.

Moreover, in the instant invention the effective dose of present synergistic composition ameliorates cellular health without any adverse effect.

'Cellular health' is the foundation of wellness, and with trillions of cells in the human body, it's critical they get the support they need. Healthy diet, regular exercise, periodic detoxification and targeted cellular health supplements help to sustain a foundation for optimal vitality throughout life.

Cellular function includes but is not limited to particular function such as mitochondrial function or cytosol function, or nucleus function or organelles function or combination thereof.

As used herein, the term "specific or effective amount" is intended to mean the therapeutically effective dose of instant bioactive compounds namely L-EGT and NMN or salts thereof in combination to give significant therapeutic efficacy, which is otherwise not obtained by use of single ingredient of the composition.

The term "pharmaceutically acceptable salt" refers to a salt prepared from pharmaceutically acceptable non-toxic acids or bases, metal ions, minerals, chelates, complex, esters, oxide, amines which are well known in the art.

As used herein, the term "pharmaceutically acceptable carriers/vehicles/diluents or excipients" is intended to mean, without limitation, any adjuvants, carriers, excipients, sweetening agents, diluents, preservative, dye/colorants, flavor enhancers, surfactants, wetting agents, dispersing agents, suspending agents, complexing agents, stabilizers, isotonic agent, solvent, emulsifier, solubilizer, encapsulating agent, polymers, coating agent, wax, encapsulating polymeric delivery systems. Excipients may also include, anti-adherents, antioxidants, binders, pH-modifier, solvents, coatings, compression aids, disintegrants, emollients, fillers (diluents), film formers, fragrances, glidants (flow enhancers), lubricants, preservatives, sorbents, anticaking agent, food additives, or waters of hydration.

In some embodiment of the invention, the diluents are selected from starches, hydrolyzed starches, and partially pregelatinized starches, anhydrous lactose, lactose monohydrate, and sugar alcohols such as sorbitol, xylitol and mannitol, cellulose powder, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, O-cyclodextrin, dextrates, dextrose, erythritol, ethylcellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like. The amount of diluent in the pharmaceutical composition/ formulation of the present invention ranges from 0.1% to 35% by wt. of the composition/formulation.

In further embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethylcellulose, guar gum, hydrogenated vegetable oil type I, hydroxyethyl cellulose, hydroxymethyl cellulose hydroxy-ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax.

The amount of binder in the pharmaceutical composition/formulation of the present invention ranges from 0.1% by wt. to 10% by wt. of the composition/formulation.

Further according to the invention, the lubricant is selected from magnesium stearate, zinc stearate, calcium stearate, glycerin monostearate, glyceryl behenate, glyceryl palmitostearate, hydrogenated castor oil, hydrogenated vegetable oil type, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition/formulation of the present invention ranges from 0.1% by wt. to 10% by wt. of the composition/formulation.

In some embodiment, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, magnesium silicate, magnesium trisilicate, silicon dioxide or the like.

The amount of glidant in the pharmaceutical composition/formulation of the present invention ranges from 0.1% by wt. to 10% by wt. of the composition/formulation.

In some embodiment, the solvent is selected from water, alcohol, isopropyl alcohol, propylene glycol, mineral oil, benzyl alcohol, benzyl benzoate, butylene glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

The amount of solvent in the pharmaceutical composition/formulation of the present invention is used in a quantity sufficient to 100% by wt. of the composition/formulation.

The additional additives include polymer, a plasticizer, a sweetener, and a powdered flavour, preservative, colorant, surfactant and other excipients. The powdered flavour composition includes a flavourant associated with a solid carrier. coating materials are used, for example synthetic polymers, shellac, corn protein zein or other polysaccharides, gelatin, fatty acids, waxes, shellac, plastics, and plant fibers and like thereof. The additives are used in the range of 1 to 50% w/w of unit dose.

Further optionally the antioxidant is selected from vitamins such as vit E, vit C, amino acid or its derivatives such as lipoid acid, uric acid, caffeic acid, acetyl-L-carnitine, ALCAR or ALC, caffeic acid and like thereof and which are present in the range of 0.5 to 5% w/w of total composition.

In the context of the present invention, the terms "treatment" and the like refer to alleviate, mitigate, prophylaxis, attenuate, manage, regulate, modulate, improve, control, minimize, lessen, decrease, down regulate, up regulate, moderate, prevent, inhibit, stabilize, ameliorate or cure, heal the indications of metabolic disorders.

The treatment further includes delaying or reversing or preventing or reducing the development or progression or formation or occurrence of conditions or indications related to metabolic disorders and/or metabolic diseases and/or metabolic syndrome or metabolic disruption or metabolic dysfunction.

Notably, the instant synergistic composition is non-hazardous, non-toxic and safe for human consumption without any side effects, therefore the instant composition can also be used under preventive therapy in healthy subjects.

The instant efficient nutritional composition is used to maintain proper metabolic function in the subject in need thereof, means the administration of the remedy either to prevent occurrence or pre-existing cause of metabolic disorders.

In another embodiment, the invention provides a method of treating a subject suffering from metabolic dysfunctions or disorders or diseases, cellular malfunctions and diseases, impairment of the mitochondrial respiratory system or other kind of damage of the mitochondrial function, the method comprising administering to the subject an efficient amount of the instant synergistic nutritional composition to enhance the cellular function, particularly.

In yet another embodiment, the invention provides a method of treating a subject suffering from diseases of mitochondrial dysfunction or disease related to mitochondrial dysfunction, the method comprising administering to the subject an efficient amount of the instant synergistic nutritional composition to enhance the mitochondrial function.

The 'subject in need thereof' pertains to subject preferably mammal, more preferably human having pre-existing or onset symptoms of metabolic disorders, like cardiovascular diseases, neurodegenerative diseases. The subject can be healthy person and use the instant composition under preventive therapy.

The therapeutically effective amount of the active ingredients may be varied depending upon the subject and disease condition being treated, the weight and age of the subject, the severity of the disease condition, the manner of administration and the like, which can readily be determined by one of ordinary skill in the art.

Thus, a "therapeutically effective" amount is an amount that reduces the risk, potential, possibility or occurrence of a disease or disorder, or provides advanced alleviation, mitigation, and/or reduction or restoration of at least one indicator/biomarker (e.g., blood or serum CRP level), and/or decrease in at least one clinical symptom of metabolic disorders (e.g. diabetes).

A skilled artisan can determine a pharmaceutically effective amount of the inventive compositions by determining the unit dose. As used herein, a "unit dose" refers to the amount of inventive composition required to produce a response of 50% of maximal effect (i.e. ED50). The unit dose can be assessed by extrapolating from dose-response curves derived from in vitro or animal model test systems.

The method of treating metabolic disorders, wherein the present composition is administered parenterally, orally, topically, buccally, sublingually, transdermally, subcutaneously, intramuscularly, via a medical device, via a stent, by inhalation or via injection.

Therapeutic (prescription) supplements are generally administered by the oral or parenteral or nasal routes for treating metabolic disorders. The therapeutic administration of materials of the present invention may be in conjunction with other therapies.

Further, the instant synergistic nutritional composition can be administered to subject in need thereof, in a form suitable for oral use, such as a tablet, capsule (in the form of delayed release, extended release, sustained release, enteric coated release); hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet or capsule, film Further the composition can be formulated for parenteral use including intravenous, subcutaneous, intramuscular, intravascular, infusion, intraperitoneal, intracerebral, intracerebroventricular, or intradermal.

In some embodiment, the invention provides a synergistic bioactive composition(s) for treating metabolic disorders, wherein the composition comprising therapeutic blend of betaine of thiol histidine and sirtuin activator(s) or salts thereof present in the ratio of 1:1 to 1:80, along with pharmaceutically acceptable excipients.

In another embodiment, the invention discloses novel synergistic nutritional composition comprising synergistic combination of bioactives L-ergothioneine and nicotinamide mononucleotide chloride present in the ratio ranges from 1:1 to 1:90.

Particularly the composition encompasses exogenous synergistic blend of L-EGT and NMN in the ratio of 1:0.5 to 1:90.

In one of the embodiment, the invention provides a method of treatment of cellular dysfunctions in a subject in need thereof, wherein the method comprising, administering to the subject a therapeutically effective amount of composition comprising exogenous synergistic blend of betaine of thiol histidine and sirtuin activator(s) or salts thereof present in the ratio of 1:0.5 to 1:90, along with pharmaceutically acceptable excipients.

In some embodiment, the invention provides a method of optimizing cellular health in a subject in need thereof, wherein the method comprising, administering to the subject a therapeutically effective amount of composition comprising exogenous synergistic blend of betaine of thiol histidine and sirtuin activator(s) or salts thereof present in the ratio of 1:1 to 1:80, along with pharmaceutically acceptable excipients. Particularly the composition encompasses exogenous synergistic blend of L-EGT and NMN in the ratio of 1:0.5 to 1:90.

In yet another embodiment, the instant composition is useful for treating cellular diseases or disorders include but are not limited to group of disorders caused by dysfunctional mitochondria, or any condition associated with oxidative stress or free radical injury such as endothelial dysfunction, aging (including senescence-associated changes in skin and appearance) and diseases like diabetes mellitus, cardiovascular diseases, neurodegenerative and neurological disorders, multiple sclerosis, convulsive (seizure) disorders, disorders of gastric secretions, relaxation and peristalsis of the intestinal tract (including inflammatory bowel diseases), pathological (premature) and physiological uterine contractions, pregnancy complications, liver diseases, kidney or renal diseases, cerebrovascular diseases, aggregation disorders, fertility and reproductive disorders (erg, penile erection and treatment of male impotence).

In another embodiment, the present invention provides synergistic bioactive composition, which is useful for treating one or more pregnancy complications such as early embryonic loss, adverse birth outcomes, pre term birth, intrauterine growth restriction (IUGR), early pregnancy loss, neural tube defects (NTD), intra-Uterine Death (IUD), pre-eclampsia (PE), oocyte quality, embryo quality, implantation, improve sperm health by reducing DNA fragmentation and increasing ATP, improve poor ovarian reserve and diminished ovarian reserve.

In some embodiment, the present invention provides synergistic composition which is useful for treating one or more liver diseases for instance hepatitis A, hepatitis B, and hepatitis C, fatty liver disease, non-alcoholic steatohepatitis (NASH) and alcoholic steatohepatitis (ASH), hemochromatosis, Wilson disease, primary biliary cirrhosis (PBC), primary sclerosing cholangitis, autoimmune hepatitis, cirrhosis, liver failure.

In additional embodiment, the present invention provides synergistic composition which is useful for treating one or more renal or kidney diseases such as acute kidney injury, chronic kidney disease, blood in urine protein in urine, kidney stones, kidney infection, kidney pain, urinary tract infections, polycystic kidney disease, inflammation, Hepatitis C and kidney disease.

In further embodiment, the invention relates to method for treating cellular dysfunction in a subject in need thereof by administering the present synergistic composition in effective oral dosage form wherein the unit dose is formulated in the range of 10-500 mg, which can be administered once or twice or thrice a day based on the indications.

The invention may be further illustrated by the following examples, which are for illustrative purposes only and should not be construed as limiting the scope of the invention in anyway. This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes or alterations which come within the ambit of equivalency are intended to be embraced therein.

Example: 1

Composition 1: Synergistic Blend

| Ingredient | Amount w/w % unit dose |
| --- | --- |
| L-(+)-Ergothioneine | 0.1-70% |
| Nicotinamide mononucleotide | 0.1-98% |

Composition 1 refers as therapeutic blend, which can be used in the preparation of present invention formulations.

Composition 1a: Synergistic Blend

| Ingredient | Amount w/w % unit dose |
| --- | --- |
| L-(+)-Ergothioneine | 5 ± 5 |
| Nicotinamide mononucleotide | 90 ± 8 |

Proprietary blend CELLSIRT1™ containing L-(+)-Ergothioneine-5.0±5.0%+Nicotinamide mononucleotide-90±8%.

Therapeutic blend with the proportionate excipients filled in soft gel, hard gel, veg capsule by known technique. The blend with the proportionate excipients is compressed to get tablet in coated or uncoated form.

Composition 2: Tablet/Capsule

| Ingredient | mg wt/unit dose |
| --- | --- |
| L-(+)-Ergothioneine | 2.5 |
| Nicotinamide mononucleotide chloride | 62.5 |
| Antioxidant | 0.5-5 |
| Excipient | 10-30 |
| Average wt. | 100 |

Composition 3: Tablet/Capsule

| Ingredient | Amount w/w % unit dose |
| --- | --- |
| L-(+)-Ergothioneine | 2.5 ± 1% |
| Nicotinamide mononucleotide chloride | 62.5 ± 1% |
| Caffeic acid | 0.5-5% |
| Diluent | 1-30% |
| Binder | 1-10% |
| Lubricant | 0.5-5% |
| Glidant | 0.5-5% |
| Additives | 1-10% |
| Solvent | Q.s. |
| Total | 100% w/w |

Composition 4: Tablet/Capsule

| Ingredient | mg per unit dose |
| --- | --- |
| L-(+)-Ergothioneine | 2.5 |
| Nicotinamide mononucleotide chloride | 62.5 |
| Acetyl l-carnitine | 4.2 |
| Microcrystalline Cellulose | 3.8 |
| Silicon dioxide | 4.5 |
| Hydroxypropyl Methylcellulose | 4.75 |
| Magnesium Stearate | 4.5 |
| PVP K-30 | 3.5 |
| Talc | 2.5 |
| Polysorbate 80 | 2.5 |
| Manitol | 4.25 |
| IPA | QS |
| Water | QS |
| Average weight | 100 mg |

The present composition is stable for 06 months under the accelerated condition [40° C., 75% RH], where the purity of the active ingredients is above 95%.

Example 2: Animal Study a. Anti-inflammatory study

Test System and Animal Husbandry

Species: Rat

Strain: Wistar; Sex: Male/Female

No. of animals: 30 Animals (n=6 per group)

Body weight: 180-200 gm

Animal House Conditions:

Lighting: 12/12 hour light-dark cycle

Temperature: 22±3° C.

Relative Humidity: 30 to 70% Temperature and relative humidity were recorded thrice daily.

Experimental Procedure

In study thirty (30) rats, were divided into total nine (09) groups.

Group 1 (G1) served as the normal control, Group 2 (G2) served as the positive control, Group 3 (G3), Group 4 (G4) and served as active ingredient L-ergothioneine and Nicotinamide mononucleotide chloride respectively Group 5 (G5), served as composition 1. G3-G4 groups are referred as test substances.

Acute anti inflammatory activity was measured using carrageenan induced rat paw edema model. Acute inflammation was induced by the sub planter administration of 0.1 ml of 1% carrageenan (0.9% NaCl solution) in the right hind paw of the rats. Group 1 was treated with normal saline. Group 2 positive control was treated with normal saline (with paw edema induction). Group 3, Group 4 and Group 5 were treated with test substance (G1—0.512 mg/kg, G2—12.33 mg/kg and G3-0.512 mg/kg+12.33 mg/kg bw) respectively. Excluding control group, all groups were pretreated 1 hr before eliciting paw edema. The linear paw circumference was measured at Time intervals: 0, 30, 60, 120, 180 and 240 mins. The perimeter of paw was measured by using vernier calipers. After the completions of the paw volume measurement animals were anesthetized and blood was collected for biochemical parameter analysis.

The anti-inflammatory activity was calculated by following formula $$\% \text{ inhibition of edema} = ((T-T0)/T) \times 100$$

T: Thickness of paw in positive control group

T0: Thickness of paw edema in the test compound treated groups.

The values were expressed in Mean±SEM. The significance of in vivo data was analyzed by One way anova followed by Dunnet test. P<0.05 was considered as statistically significant Results:

TABLE 1

Effect of Test substances on Percentage inhibition of paw edema

| Group | Treatment | % inhibition of paw edema at 6$^{th}$ hr. |
|---|---|---|
| G1 | Normal control | ... |
| G2 | Positive control | ... |
| G3 | L-Ergothioneine | 35.08% |
| G4 | Nicotinamide mononucleotide chloride | 40.80% |
| G5 | Composition 1a | 46.02% |

TABLE 2

Effect of test substances on serum IL-6 levels

| Group | Treatment | IL-6(pg/ml) | Percentage inhibition over control |
|---|---|---|---|
| G1 | Normal control | 66.28 ± 0.35 | ... |
| G2 | Positive control | 101.2 ± 0.90 | ... |
| G3 | L-Ergothioneine | 85.25 ± 0.30*** | 15.74% |
| G4 | Nicotinamide mononucleotide chloride | 79.55 ± 0.95*** | 21.34% |
| G5 | Composition 1a | 75.52 ± 0.30*** | 25.35% |

TABLE 3

Effect of test substances on serum TNF-Alpha levels

| Group | Treatment | TNF-Alpha (pg/ml) | Percentage inhibition over control |
|---|---|---|---|
| G1 | Normal control | 156.5 ± 1.04 | ... |
| G2 | Positive control | 232.4 ± 3.04 | ... |
| G3 | L-Ergothioneine | 201.5 ± 1.96*** | 13.21% |
| G4 | Nicotinamide mononucleotide chloride | 185.2 ± 4.37*** | 20.18% |
| G5 | Composition 1a | 179.2 ± 1.62*** | 22.79% |

DISCUSSION

In this study, Carrageenan induced acute inflammation test was used to screen the anti-inflammatory effect.

Table-01 shows the time course of edema and inhibition rate after the administration of tests substance at different time interval. (G3), (G4) and the combination of both (G5) treated groups showed significant decreases paw edema when compared with Positive control group (G2).

The composition 1 (G5) (40.98%) treated groups showed better percentage inhibition of paw edema when compared with positive control group (G2). The biochemical parameter such as Serum interleukin-6 and TNF-Alpha significantly decreased in (G3), (G4) and the combination of both (G5) treated groups when compared with positive control (G2) (Table 2 and 3). The combination of L-EGT and NMN (G5) treated groups showed significantly decreases the paw edema volume, better percentage inhibition of paw edema and decreased serum interleukin-6 and TNF-Alpha level when compare with (G3) and (G4).

Conclusion: Based on the above trials, it is concluded that the combination of L-EGT and NMN chloride (G5) showed better anti-inflammatory activity than test substances (G3) and (G4).

b. In Vitro Cytotoxicity Studies and DNA Fragmentation in HepG2 Cells

In-vitro cytotoxicity of the nutrients, G3, G4 and G5 were tested against HepG2 cell line. Nutrients were taken at concentrations ranging from 1000 µg/ml to 62.5 µg/ml to determine the percentage growth inhibition of individual substance on HepG2 cell line. The samples G3 and G4 produced a CTC50 value of above 1000 µg/ml. The test substances G3 and G4 were subjected to DNA fragmentation studies and at concentration (250 µg/ml) did not exhibit any fragmentation of DNA. [Journal of Immunological Methods, 1986; 89:271-277].

Procedure:

i. Outline of the Method

The in vitro cytotoxicity was performed for samples G3, G4 and G5 on HepG2 to find toxic concentration and to determine the apoptotic activity of G3, G4 and G5.

ii. Preparation of Test Solution

For cytotoxicity studies, 10 mg of test substance was separately dissolved and volume was made up with MEM supplemented with 2% inactivated FBS to obtain a stock solution of 1 mg/ml concentration and sterilized by 0.22µ syringe filtration. Serial two fold dilutions were prepared from this for carrying out cytotoxic studies.

iii. Cell Line and Culture Medium:

HepG2 (Human Hepatocyte) cell line was procured from National Centre for Cell Sciences (NCCS), Pune, India. Stock cells were cultured in MEM supplemented with 10% inactivated Fetal Bovine Serum (FBS), penicillin (100 IU/ml), streptomycin (100 µg/ml) and amphotericin B (5 µg/ml) in an humidified atmosphere of 5% $CO2$ at 7° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 microtitre plates (Tarsons India Pvt. Ltd., Kolkata, India).

iv. Cytotoxicity Studies:

The monolayer cell culture was trypsinized and the cell count was adjusted to 100,000 cells/ml using DMEM-HG containing 10% FBS. To each well of the 96 well microtitre plate, 0.1 ml of the diluted cell suspension was added. After 24 h, when a partial monolayer was formed, the supernatant was flicked off, washed the monolayer once with medium and 100 µl of different test concentrations of test substances were added on to the partial monolayer in microtitre plates. The plates were then incubated at 37° C. for 3 days in 5% $CO_2$ atmosphere, and microscopic examination was carried out and observations were noted every 24 h interval. After 72 h, the substance solutions in the wells were discarded and 50 µl of MTT in PBS was added to each well. The plates were gently shaken and incubated for 3 h at 37° C. in 5% CO2 atmosphere. The supernatant was removed and 100 µl of propanol was added and the plates were gently shaken to solubilize the formed formazan. The absorbance was measured using a microplate reader at a wavelength of 540 nm. The percentage growth inhibition was calculated using the standard formula and concentration of test substance needed to inhibit cell growth by 50% ($CTC_{50}$) values is generated from the dose-response curves for each cell line.

v. DNA Fragmentation Studies

HepG2 cells (3×106/ml) were seeded into 60 mm petri dishes and incubated at 37° C. with 5% CO2 atmosphere for 24 h. The cells were washed with medium and were treated with extract, standard substance and incubated at 37° C., 5% CO2 for 24 hrs. At the incubation time ended, the chromosomal DNA of cancer cells was prepared with G Biosciences, USA apoptotic DNA ladder kit. Total genomic DNA was extracted and resolved on a 1% agarose gel. Apoptotic DNA fragmentation was visualized by ethidium bromide staining under UV transilluminator and photographed. (FIG. 3)

Results:

TABLE 1

Cytotoxic properties of test substance against HepG2 cell line

| SI No. | Name of Test Compound | Test Conc. (µg/ml) | % Inhibition | CTC 50 in µg/ml |
|---|---|---|---|---|
| 1 | G3 | 1000 | 29.97 ± 1.52 | >1000 |
|   |    | 5000 | 22.34 ± 0.96 |   |
|   |    | 250  | 19.03 ± 1.05 |   |
|   |    | 125  | 10.99 ± 1.31 |   |
|   |    | 62.5 | 6.62 ± 0.88  |   |
| 2 | G4 | 1000 | 31.49 ± 0.79 | >1000 |
|   |    | 500  | 24.19 ± 1.59 |   |
|   |    | 250  | 17.56 ± 1.16 |   |
|   |    | 125  | 11.15 ± 3.32 |   |
|   |    | 62.5 | 5.26 ± 1.5   |   |
| 3 | G5 | 1000 | 41.32 ± 3.77 | >1000 |
|   |    | 500  | 27.08 ± 1.43 |   |
|   |    | 250  | 22.92 ± 1.5  |   |
|   |    | 125  | 13.72 ± 2.5  |   |
|   |    | 62.5 | 7.26 ± 1.4   |   |

DISCUSSION AND CONCLUSION

The percentage growth inhibition was calculated and concentration of substances i.e., G3 and G4 needed to inhibit cell growth by 50% (CTC50) values was generated from the dose-response curves for the cell line. The test substances G3 and G4 showed a CTC50 value above 1000 µg/ml. Hence, 250 µg/ml concentration was chosen for carrying out DNA fragmentation in HepG2 cells. The untreated and test substance treated cells showed no DNA fragmentation. AAPH treated sample showed a smear in the gel indicating the DNA fragmentation.

The present composition exhibit around 45% growth inhibition in hepatotoxic cells.

Example 3: In Vitro Gene Expression Studies on Nrf2

The test substances were evaluated for its In vitro gene expression activity in Human Hepatocyte cell line, the test substances were evaluated for cytotoxicity with different concentrations from 1000-62.5 µg/ml. The test substances exhibited a $CTC_{50}$ value greater than 1000 µg/ml on the HepG2 cells and hence lower CTC50 concentration were taken for Gene expression studies. In gene expression study, the test substance at lower concentration (250 µg/ml) showed up regulation in the level of Nrf2 gene as compared to the control. [Ref: *Investigative Ophthalmology & Visual Science*, April 2008, Vol. 49, No. 4]

Procedure:

i. Outline of the Method

Nrf2 were estimated for the test substance by gene expression method, where the level of expression of Nrf2 expression on Human Hepatocytes (HepG2) was determined with respect to untreated HepG2 cells.

ii. Preparation of Test Solution

For cytotoxicity studies, 10 mg of test substance powder was separately dissolved and volume was made up with DMEM supplemented with 2% inactivated FBS to obtain a stock solution of 10 mg/ml concentration and sterilized by 0.22µ syringe filtration. Serial two fold dilutions were prepared from this for carrying out cytotoxic studies.

iii. Cell Line and Culture Medium

HepG2 (Human Hepatocyte) cell line was procured from National Centre for Cell Sciences (NCCS), Pune, India. Stock cells were cultured in DMEM supplemented with 10% inactivated Fetal Bovine Serum (FBS), penicillin (100 IU/ml), streptomycin (100 µg/ml) and amphotericin B (5 µg/ml) in an humidified atmosphere of 5% CO2 at 37° C. until confluent. The cells were dissociated with TPVG solution (0.2% trypsin, 0.02% EDTA, 0.05% glucose in PBS). The stock cultures were grown in 25 cm2 culture flasks and all experiments were carried out in 96 microtitre plates (Tarsons India Pvt. Ltd., Kolkata, India).

iv. Cytotoxicity Studies

The monolayer cell culture was trypsinized and the cell count was adjusted to 100,000 cells/ml using medium containing 10% FBS. To each well of the 96 well microtitre plate, 0.1 ml of the diluted cell suspension was added. After 24 h, when a partial monolayer was formed, the supernatant was flicked off, washed the monolayer once with medium and 100 µl of different test concentrations of test substance powder was added on to the partial monolayer in microtitre plates. The plates were then incubated at 37° C. for 3 days in 5% CO2 atmosphere, and microscopic examination was carried out and observations were noted every 24 h interval. After 72 h, the drug solutions in the wells were discarded and 50 µl of MTT in PBS was added to each well. The plates were gently shaken and incubated for 3 h at 37° C. in 5% $CO_2$ atmosphere. The supernatant was removed and 100 µl of DMSO was added and the plates were gently shaken to solubilize the formed formazan. The absorbance was measured using a microplate reader at a wavelength of 540 nm. The percentage growth inhibition was calculated and concentration of test drug needed to inhibit cell growth by 50% ($CTC_{50}$) values is generated from the dose-response curves for each cell line.

v. RNA Isolation and cDNA Synthesis

The HepG2 cells treated with drug were subjected to cell lysis by treating with Tri-extract reagent. Chloroform was added, to isolate the total RNA from the sample and subjected for centrifugation. Out of the three distinct layers observed, upper layer was collected in fresh tube and equal volume of isopropanol was added and incubated at −20° C. for 10 mins. After the incubation followed by centrifugation, appropriate volume of ethanol was added to resuspend the pellet. After incubation and centrifugation, the pellet was air dried and appropriate volume of TAE buffer was added. The isolated total RNA was further used for cDNA synthesis. cDNA was synthesized by priming with oligo dT primers followed by reverse transcriptase enzyme treatment according to manufacturer's protocol (Thermo scienctific). The cDNA thus synthesized was taken up for Polymerase chain reaction (PCR) for the amplification of Nrf2 and Glyceraldehyde 3-phosphate dehydrogenase GAPDH (internal control).

vi. RT-PCR Procedure

The mRNA expression levels of Nrf2 were determined using semi-quantitative reverse transcriptase-polymerase chain reaction (RT-PCR). 50 µl of the reaction mixture was subjected to PCR for amplification of Nrf2. cDNAs using specifically designed primers procured from Eurofins, India and as an internal control GAPDH (House keeping gene) was co-amplified with each reaction.

vii. Amplification Conditions for Nrf2 Gene

Nrf2: 95° C. for 5 min followed by 35 cycles of denaturation at 95° C. for 30 seconds, annealing Tm for 30 seconds and extension at 72° C. for 45 seconds. This was followed by final extension at 72° C. for 10 min.

The primers used in this example for I strand synthesis and II nd strand synthesis are disclosed in priority Indian Patent Application No. 201821045886, filed Dec. 5, 2018, which is incorporated herein by reference.

Product size: 118 bp.

Results

TABLE 2

The gene expression level of Nrf2 normalized to GAPDH

| Test Sample | Regulation in Terms of Folds |
| --- | --- |
| Cell Control | 1.00 |
| G3 | >1.0 |
| G4 | >1.0 |
| G5 | >1.0 |

DISCUSSION AND CONCLUSION

A Reverse Transcriptase-PCR experiment was performed by using Nrf2-specific primers. Quantitative RT-PCR analysis revealed that Nrf2 mRNA was increased by test substance treatment (250 μg/ml) compared to the cells control (untreated). There was a notable difference between the mRNA levels of Nrf2 in the cells treated with test substance compared to the cell controls. The presence of test substance produced an increase of Nrf2 mRNA expression in test substance-treated cells. The present composition up regulates the Nrf2 expression by 40 to 70% as compared to control.

We claim:

1. A method for increasing Nrf2 gene expression, the method comprising: administering to a subject a therapeutically effective amount of a composition comprising active ingredients and pharmaceutically acceptable excipients, wherein the active ingredients consist of L-ergothioneine and beta-nicotinamide mononucleotide in a weight ratio of 1:10 to 1:25.

2. The method according to claim 1, wherein the L-ergothioneine is present in a range of 1% to 10% by weight of the total composition.

3. The method according to claim 1, wherein the beta-nicotinamide mononucleotide is present in a range of 10% to 98% by weight of the total composition.

4. The method according to claim 1, wherein the composition further comprises caffeic acid in a range of 0.1% to 10.0% by weight of the total composition.

5. A synergistic bioactive composition(s) for increasing Nrf2 gene expression, the composition comprising: active ingredients and pharmaceutically acceptable excipients, wherein the active ingredients consist of L-ergothioneine and beta-nicotinamide mononucleotide in a weight ratio of 1:10 to 1:25.

6. The synergistic bioactive compositions according to claim 5, wherein the L-ergothioneine is present in a range of 1% to 10% by weight of the total composition.

7. The synergistic bioactive compositions according to claim 5, wherein the beta-nicotinamide mononucleotide is present in a range of 10% to 98% by weight of the total composition.

8. The synergistic bioactive compositions according to claim 5, wherein the composition comprises amino acid or its derivatives, uric acid, and caffeic acid present in a range of 0.1% to 10.0% by weight of the total composition.

9. The synergistic bioactive compositions according to claim 5, wherein the pharmaceutically acceptable excipients are selected from a diluent, a binder, a lubricant, a glidant, an additive, solvent or mixture thereof; wherein the amount of diluent ranges from 1-30%; the amount of binder ranges from 1-10%; the amount of lubricant ranges from 0.5-5%; the amount of glidant ranges from 0.5-50%; the amount of additive ranges from 1-10% by weight of the total composition.

10. The synergistic bioactive compositions according to claim 5, wherein the administration of the effective dose of the composition increases production of ATP in the subject in need thereof.

11. The synergistic bioactive compositions according to claim 5, wherein the administration of the effective dose of the composition reduces inflammation in a subject in need thereof.

12. A synergistic nutritional composition for increasing Nrf2 gene expression, the composition comprising a combination of L-ergothioneine and beta-nicotinamide mononucleotide in a weight ratio of 1:10 to 1:25.

* * * * *